United States Patent
Gingrich et al.

(10) Patent No.: US 10,410,439 B1
(45) Date of Patent: Sep. 10, 2019

(54) DETERMINING AND ASSESSING POST-ACCIDENT VEHICLE DAMAGE

(71) Applicant: UNITED SERVICES AUTOMOBILE ASSOCIATION (USAA), San Antonio, TX (US)

(72) Inventors: Jess W. Gingrich, San Antonio, TX (US); Carlos J. Chavez, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 224 days.

(21) Appl. No.: 15/287,838

(22) Filed: Oct. 7, 2016

Related U.S. Application Data

(60) Provisional application No. 62/239,662, filed on Oct. 9, 2015.

(51) Int. Cl.
| | | |
|---|---|---|
| *G07C 5/08* | (2006.01) | |
| *G01C 21/34* | (2006.01) | |
| *G01N 29/44* | (2006.01) | |
| *G01N 29/06* | (2006.01) | |
| *G06Q 40/08* | (2012.01) | |

(52) U.S. Cl.
CPC ....... *G07C 5/0808* (2013.01); *G01C 21/3407* (2013.01); *G01N 29/069* (2013.01); *G01N 29/4445* (2013.01); *G06Q 40/08* (2013.01); *G01N 2291/0289* (2013.01)

(58) Field of Classification Search
None
See application file for complete search history.

(56) References Cited

U.S. PATENT DOCUMENTS

| | | | | |
|---|---|---|---|---|
| 5,629,681 A | * | 5/1997 | DuVall | B60J 10/00 340/665 |
| 6,386,038 B1 | * | 5/2002 | Lewis, III | G01N 29/14 702/39 |
| 6,957,582 B1 | * | 10/2005 | Durkee | G01F 23/2962 310/319 |
| 9,721,400 B1 | * | 8/2017 | Oakes, III | G07C 5/0808 |
| 2007/0288135 A1 | * | 12/2007 | Kidd | G01C 11/06 701/31.4 |
| 2008/0255887 A1 | * | 10/2008 | Gruter | G06Q 40/08 705/4 |
| 2014/0081675 A1 | * | 3/2014 | Ives | G06Q 40/08 705/4 |
| 2014/0278571 A1 | * | 9/2014 | Mullen | G06Q 40/08 705/4 |
| 2014/0278572 A1 | * | 9/2014 | Mullen | G06Q 40/08 705/4 |
| 2015/0033864 A1 | * | 2/2015 | Kumar | G01N 29/265 73/636 |
| 2016/0292759 A1 | * | 10/2016 | Gonzalez Miranda | G06Q 30/0611 |
| 2017/0352104 A1 | * | 12/2017 | Hanson | G06Q 30/0283 |

FOREIGN PATENT DOCUMENTS

| | | | | | |
|---|---|---|---|---|---|
| DE | 102006051246 A1 | * | 5/2008 | | G01N 29/11 |
| KR | 20090028258 A | * | 3/2009 | | |

* cited by examiner

*Primary Examiner* — Shelley Chen
(74) *Attorney, Agent, or Firm* — Baker & Hostetler LLP

(57) ABSTRACT

The present disclosure provides systems, machine-readable media, and methods for detecting and assessing damage to a motor vehicle. One or more embodiments include dispositioning the motor vehicle based on the detected damage using a repair/scrap threshold.

11 Claims, 3 Drawing Sheets

DETERMINING AND ASSESSING POST-ACCIDENT VEHICLE DAMAGE

CROSS REFERENCE TO RELATED APPLICATIONS

This application claims priority to and incorporates by reference herein U.S. Ser. No. 62/239,662 filed Oct. 9, 2015.

FIELD OF THE INVENTION

The disclosed embodiments generally relate to methods and computerized systems for assessing post-accident damage to a vehicle, and more particularly, to using non-destructive data acquired from a vehicle post-accident to disposition the vehicle based on an assessment of the damage resultant from an accident.

BACKGROUND OF THE INVENTION

Non-destructive inspection and testing techniques are commonly used for determining the condition of mechanical elements and systems, but the opportunity for insurance companies to apply non-destructive testing techniques remains largely untapped. Currently, there are few useful non-destructive inspection systems and methods that allow assessing vehicular damage prior to dispositioning a damaged vehicle for repair from the site of an accident. Such systems and methods could reduce costs for both the insured and the insurer by reducing the need to move a damaged vehicle more than once during the repair process, for example as would be the circumstance when a repair shop determines that a vehicle initially determined as repairable is in fact not economically repairable.

BRIEF DESCRIPTION OF THE DRAWINGS

The accompanying drawings illustrate various non-limiting, exemplary, inventive aspects in accordance with the present disclosure.

DETAILED DESCRIPTION OF CERTAIN EMBODIMENTS

Figure 1:
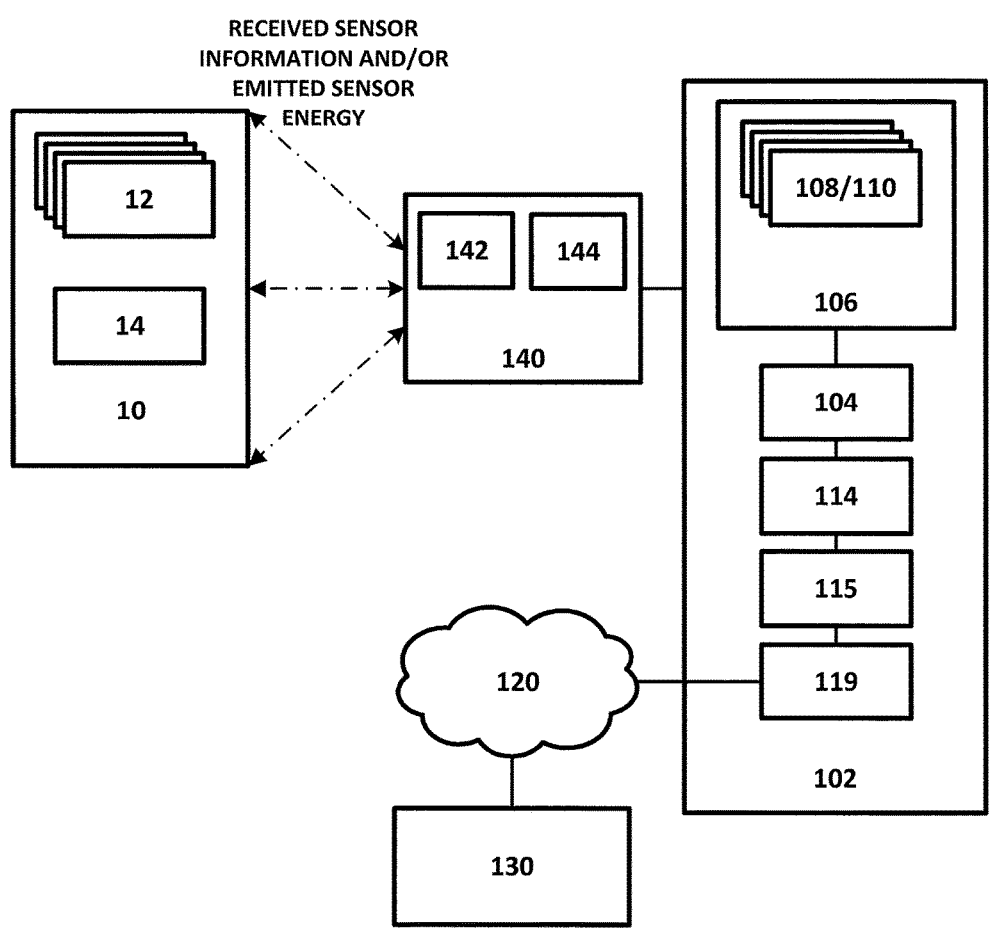
FIG. 1 illustrates an example of a system for detecting damage to a motor vehicle and dispositioning the motor vehicle for repair or scrap according to one or more embodiments of the present disclosure.

The illustrated embodiments are now described more fully with reference to the accompanying drawings wherein like reference numerals identify similar structural/functional features. The illustrated embodiments are not limited in any way to what is illustrated as the illustrated embodiments described below are merely exemplary, which can be embodied in various forms, as appreciated by one skilled in the art. Therefore, it is to be understood that any structural and functional details disclosed herein are not to be interpreted as limiting, but merely as a basis for the claims and as a representation for teaching one skilled in the art to variously employ the discussed embodiments. Furthermore, the terms and phrases used herein are not intended to be limiting but rather to provide an understandable description of the illustrated embodiments.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the illustrated embodiments, exemplary methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "a stimulus" includes a plurality of such stimuli and reference to "the signal" includes reference to one or more signals and equivalents thereof known to those skilled in the art, and so forth.

It is to be appreciated the illustrated embodiments discussed below may include a software algorithm, program or code residing on computer useable medium having control logic for enabling execution on a machine having a computer processor. The machine can include memory storage configured to provide output from execution of the computer algorithm or program.

As used herein, the term "software" is meant to be synonymous with any code or program that can be in a processor of a host computer, regardless of whether the implementation is in hardware, firmware or as a software computer product available on a disc, a memory storage device, or for download from a remote machine. The embodiments described herein include such software to implement the equations, relationships and algorithms described above. One skilled in the art will appreciate further features and advantages of the illustrated embodiments based on the above-described embodiments. Accordingly, the illustrated embodiments are not to be limited by what has been particularly shown and described, except as indicated by the appended claims. All publications and references cited herein are expressly incorporated herein by reference in their entirety.

The term "motor vehicle" refers to any motorized vehicles capable of self-propulsion including, for example, automobiles, motorcycles, boats, recreational vehicles, et cetera. Motor vehicles include motor vehicle components. The term "motor vehicle component" refers to a constituent part of a motor vehicle. Motor vehicle components can include, e.g., doors, fenders, engines (as a whole or components thereof such as blocks, pistons, belts, et cetera), computer panels (as a whole or components thereof such as processors, memory, displays, et cetera), chassis elements, et cetera, that provide a function and/or a desired configuration (e.g., an aesthetically desirable configuration) of the motor vehicle. The motor vehicle components can be located on an interior and/or on an exterior of the motor vehicle. The motor vehicle component can be included in and/or comprise a mechanical systems of the motor vehicle, for example, a drive train, and engine (e.g., a component of an engine), a blinker, a headlight, a tire, a frame, among other mechanical systems that can perform a mechanical function to enable the motor vehicle to operate/perform as intended. The motor vehicle components can be made of steel, metal alloys, electronics, composite materials (e.g., plastics, resins, et cetera), among other materials and/or combinations of materials.

It is understood that motor vehicles are frequently damaged due to collisions, weather events, vandalism, et cetera. It can be desirable to repair a motor vehicle by replacing one or more motor vehicle components to restore a given function and/or motor vehicle configuration subsequent to sustaining damage, such as from an accident. Repair can include replacement of a motor vehicle component and/or alteration of motor vehicle components. For example, it may be desirable to replace a damaged motor vehicle component. The cost and components for repair will frequently be a result of the mechanism of damage. Damage can occur in a variety of ways such as exposure to environmental elements (e.g., light, heat, hail, et cetera), as a result of a force applied to the motor vehicle/motor vehicle component (e.g., resultant forces from an automobile accident), and/or vandalism (e.g., windows broken, panels scratched or "keyed," tires slashed, et cetera) among other ways. Depending on an amount of damage sustained and consequent cost of repairs to restore the vehicle to a serviceable or undamaged state, a damaged motor vehicle component may be a candidate for replacement. For instance, it may be desirable to replace a damaged motor vehicle component where the expense of repair exceeds the value of the motor vehicle, or where the extent of required repairs would deprive an owner of a vehicle for an unnecessarily long period of time.

Detecting motor vehicle damage in-situ, at the site of an accident for example, can expedite response to the damage and reduce inefficiency from delay or improper response management. For example, detecting motor vehicle damage to ascertain the extent of the damage can provide determination of whether a motor vehicle can be repaired or has damage significant enough to require "scrapping" the vehicle. As used herein, "scrapping" the vehicle can include making a determination to disposition the vehicle as a total loss, described hereafter. Since it increases cost and delay to both an insured and an insurer to transport a damaged vehicle to a repair shop when the vehicle has sustained damage significant enough to warrant scrapping the vehicle, the decision to disposition the vehicle for repair or scrap may be made at the site of the vehicle accident and prior to recovering the vehicle to a repair facility when the scrapping is warranted.

The present disclosure provides methods, systems, and computer-readable and executable instructions for detecting damage to a motor vehicle, and correctly and efficiently dispositioning the motor vehicle based on the detected damage. Detecting the damage to the motor vehicle, in accordance with one or more embodiments, can include detecting an amount or character of damage to one or more motor vehicle components of the motor vehicle. The amount or character of damage can be described in terms of relative or absolute qualities or quantities capturing functionality, safety, aesthetics, and cost. Damage can be detected by a sensor, such as those described herein, or inferred based on data received therefrom. Assessing damage may include receiving data from the sensor indicative of the damage. Aspects herein can also include dispositioning the motor vehicle based upon a repair/scrap threshold associated with the motor vehicle.

The embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

The figures herein follow a numbering convention in which the first digit or digits correspond to the drawing figure number and the remaining digits identify an element or component in the drawing. Similar elements or components between different figures may be identified by the use of similar digits. As used herein, "a" or "a number of" something can refer to one or more such things. For example, "a number of objects" can refer to one or more objects.

Referring now to FIG. 1, a motor vehicle is generally indicated by reference numeral 10. Motor vehicles refer to motorized vehicles capable of self-propulsion including, for example, automobiles, motorcycles, boats, recreational vehicles, et cetera. As used herein self-propulsion need not be synonymous with self-driving, instead meaning that means for moving the vehicle (e.g., motor or engine and components driven thereby) are contained in or on, or otherwise operatively coupled with, the vehicle. While aspects herein discuss motor vehicles, it is understood that aspects herein can be extended to other vehicles or properties subject to insurance policies where similar assessment and dispositioning occurs (e.g., a camper is a non-motorized vehicle but may still be insured and subject to repair/scrap thresholds).

The motor vehicle 10 can include a plurality of motor vehicle components 12. Motor vehicle components 12 refer to constituent parts of a motor vehicle, such as doors, fenders, engines, computer panels, et cetera, that provide a function and/or a desired configuration (e.g., an aesthetically desirable configuration) of the motor vehicle.

The motor vehicle components 12 can be located on an interior and/or on an exterior of the motor vehicle 10. The motor vehicle components 12 can be made of steel, metal alloys, electronics, composite materials (e.g., plastics, resins, et cetera), among other materials and/or combinations of materials. Among the motor vehicle components 12 is a motor vehicle frame 14, which generally supports one or more of motor vehicle components 12. As will be appreciated, motor vehicle frames can absorb sufficient energy in motor vehicle to undergo a change in shape. As will also be appreciated, change in the shape of a motor vehicle frame generally changes the acoustic response of the frame to input sound. As further explained below, the magnitude of the change response to a predetermined input sound can be correlated to the cost to repair damage to the motor vehicle, such as be comparing reflected sound to a baseline of reflected sound (e.g., baseline acoustic response information).

Also shown in FIG. 1 is a system for detecting damage to a motor vehicle, generally indicated by reference numeral 100. System 100 includes a mobile device 102. Mobile device 102 can include a processor 104 and a memory 106. Memory 106 can be any type of storage medium that can be accessed by the processor 104 to perform various embodiments of the present disclosure (e.g., provide an indication of an amount of damage to a motor vehicle component, et cetera). For example, memory 106 can be a non-transitory machine readable medium having machine readable instructions 110 (e.g., generating machine program instructions, machine readable instructions, computer readable instructions, et cetera) and data items 108 stored thereon, such as within one or more program modules. Memory 106 can be volatile or nonvolatile memory. Memory 106 can also be removable (e.g., portable) memory, or non-removable (e.g., internal) memory. For example, memory 106 can be random access memory (RAM) (e.g., dynamic random access memory (DRAM) and/or phase change random access memory (PCRAM)), read-only memory (ROM) (e.g., electrically erasable programmable read-only memory (EE- PROM) and/or compact-disc read-only memory (CD-ROM)), flash memory, a laser disc, a digital versatile disc (DVD) or other optical disk storage, and/or a magnetic medium such as magnetic cassettes, tapes, or disks, among other types of memory.

The memory 106 can include machine readable instructions 110 capable of being executed by the processor 104 to carry out the functions as described herein. In some embodiments, some or all of the functions are carried out via hardware in lieu of a processor-based system. Further, although memory 106 is illustrated as being located in the mobile device, alternative or complementary embodiments of the present disclosure are not so limited. For example, in addition or alternative to the memory located in the mobile device 102, memory 106 can be located internally within another computing resource (e.g., enabling computer readable instructions to be downloaded over a wired or wireless connection).

The processor 104 executes instructions, such as machine readable instructions 110, and can, in some generating machines, be utilized to control the operation of an entire generating machine (e.g., a system which uses known, received, or sensed information to generate and compare models of undamaged and damaged motor vehicles or components thereof) and/or control one or more sensors 140, among others machines and/or components (e.g., components included in the mobile device 102). The processor 104 can include a control unit that organizes data and program storage in memory and transfers data and/or other information between the various portions of the mobile device 102, a generating machine, as described herein, and/or other electronic devices. Although the mobile device 102 is shown to contain a single processor 104, the disclosed embodiment also applies to devices that may have multiple processors with some or all performing different functions and/or in different ways. The machine readable instructions 110 can, for example, include a number of programs such as the applications (e.g., software objects and/or modules, among others). The data items 108, such as information associated with a motor vehicle component and/or an electronic model, can be used (e.g., analyzed by) the machine readable instructions 110 during their execution.

As illustrated in FIG. 1, the mobile device 102 may include a sensor 140 operatively connected to mobile device 102. While one sensor 140 is illustrated, it is understood multiple sensors can be utilized without departing from the scope or spirit of the innovation. Sensors refer to devices that can detect sensory input. Sensors can include, for example, accelerometers, optical measurement devices, visual sensors, such as those described herein, material sensors (e.g., nano-material detection sensors), and/or electromagnetic frequency (EMF) sensors, among other types of sensors. The present subject matter is not limited to any particular type of sensor, as various sensors may be used as a sensor of the plurality of sensors 140 and are considered within the scope of the present subject matter.

In embodiments, a sensor of the plurality of sensors 140 can detect acoustic data (e.g., data compared to a baseline indicating a change) associated with the motor vehicle component to detect damage (e.g., damage to the motor vehicle component like frame 14). A change in the acoustics of a particular motor vehicle component (e.g., compared to a baseline acoustics associated with the particular motor vehicle component) can indicate that damage has occurred, for instance, damage to the motor vehicle component has altered its shape and/or acoustic frequency.

Sensor 140 can include the capability to send and receive information and/or energy, and may be active or passive in this regard. In this regard, a sensor may include sub-elements such as at least one emission component 142 and at least one reception component 144. Emission component 142 can generate and/or emit energy used by sensor 140 to create a signal to discern sensory information. Reception component 144 can receive information to discern sensory information, either consequent to energy emitted by sensor 140 (for active sensors such as acoustic sensors, material sensors, EMF sensors, et cetera) or pre-existing in the environment (for passive sensors such as cameras, thermometers, accelerometers, et cetera).

In an embodiment, sensor 140 can be an acoustic sensor configured to emit acoustic energy using emission component 142 and receive acoustic energy reflected back from its emission using reception component 144. To improve the quality of feedback, sensor 140 can include an ambient noise filter which leverages reception component 144 to determine ambient noise not related to the acoustic emission emitted by emission component 142 and filter such ambient noise from the acoustic information collected by the reception component 144.

Sensor 140 among a plurality of sensors can also leverage other sensor data to produce information for analysis and evaluation. For example, in embodiments where sensor 140 is an acoustic sensor, various other sensors can be used, alone or in conjunction with a user interface, to assist with accurate employment of acoustic sensor 140. For example, additional emission components, cameras, and dedicated (e.g., global positioning system) or incidental (e.g., wireless receiver leveraged for triangulation or other mobile location techniques) location systems to ensure known positioning prior to processing acoustic feedback. In an embodiment, adjustments can be made to a processing algorithm to account for a specific positioning of a sensor in relation to a vehicle or target. In an alternative embodiment, a user interface may provide instructions or directions for positioning and orienting sensor 140 (or associated components) prior to receiving or processing acoustic information (e.g., showing where to position the sensor or giving relative or absolute directional information for repositioning). Sensors can also be used to determine contextual factors which can influence the acoustic information gathered, such as the presence of passengers, luggage, or other variables which will influence the acoustic information gathered.

Further, additional sensors can be used to augment or supplement information from sensor 140, either to determine damage or refine data from another sensor. For example, a camera can take a picture of a current state of a vehicle which is compared to earlier baseline pictures or stock pictures of the vehicle in undamaged condition. Sensors can further collect not only post-damage information, but accident related information in real-time, to the extent that they are passively engaged prior to an accident. In one example, an accelerometer in a mobile device 102 (or motor vehicle 10 communicatively coupled therewith) can detect the acceleration or deceleration and estimate damaged based thereon. Where multiple types of sensor data are available, the data can be combined or averaged to determine more accurate information related to events and damage. In embodiments, sensor data can be weighted based on its type (e.g., acoustic information used in acoustic analysis weighted higher than photo information used in image recognition), quality (e.g., acoustic analysis weighted higher than blurry or dark photo), damaged component of the vehicle or sensor target (e.g., engine as opposed to window), or other characteristics. The weighted amounts can be used in averaging or other combining of disparate sensor data to arrive at more detailed damage information.

In embodiments, sensor 140 can be integral to mobile device 102. Additional sensors may also be integral to mobile device 102. In embodiments, additional sensors may be integral to other systems, such as a motor vehicle or traffic signal, and operatively coupled with mobile device 102 or other components described herein. In alternative or complementary embodiments, sensor 140 or other sensors may be non-integral and communicatively coupled with mobile device 102 or other elements in communication therewith using wired or wireless connection means.

In various embodiments, information associated with a plurality of motor vehicle components, among other information, can be stored in a data store 130. Data store can include memory as described herein and/or a database, among other suitable types of storage. In some embodiments, the data store 130 can be located within a mobile device 102. A data store located in a mobile device 102 can, for example, include information associated with some (e.g., exterior components) or all of the motor vehicle components (e.g., all exterior and interior motor components) of the mobile device 102.

The data store 130 can, in some embodiments, include information associated with all motor vehicle components that do not include electronics embedded therein. In some embodiments, the data store 130 can include information associated with a component indicated as a damaged component. In some embodiments, the data store 130 can be located within the mobile device 102 and/or can include respective information to generate each of a plurality of motor vehicle components (e.g., external components and/or internal components) included in a mobile device 102.

While the data store 130 can be located within a mobile device 102, the present disclosure is not so limited. For example, the data store 130 can be located at a shop (e.g., a repair shop capable of replacing a damaged motor vehicle component with a generated motor vehicle component) and/or a location associated with an insurance provider (e.g., an insurance provider of the mobile device 102), among other locations. In some embodiments, the data store 130 can be located a separate and distinct location from a mobile device 102 at a time of generation of a motor vehicle component (e.g., a 3D copy of a motor vehicle component). Advantageously, this can enable generation of the motor vehicle component by a number of possible entities including those located at a separate and distinct location from the motor vehicle and/or a shop scheduled to receive a motor vehicle component following generation of the motor vehicle component, among other advantages. For instance, in some embodiments, the data store 130 can include an electronic model of a motor vehicle component indicated as damaged.

The data store 130 can include information to generate (e.g., model or represent quantitatively or qualitatively) components for a plurality of types (e.g., makes) of motor vehicles. For example, a data store(s) at a location associated with an insurance provider can include information associated with generating components for a plurality of types of vehicles the insurance provider provides insurance to. That is, in some embodiments, the data store 130 can be located, external to the mobile device 102, for instance, at a location associated with an insurance provider providing insurance to the mobile device 102.

The information associated with the motor vehicle component can include a manufacturer (e.g., OEM or non-OEM), an identifier of the motor vehicle component (e.g., a motor vehicle component number), an expected life (e.g., an average duration of useful life of a motor vehicle component), a status (e.g., current status) of the motor vehicle component, a type of material, specifications, an indicator of a presence of electronics embedded within the motor vehicle component, among other information that can be associated with the motor vehicle component. For example, in some embodiments, a data store can include respective information identifying a manufacturer of each of the plurality of motor vehicle components included in the motor vehicle. In some embodiments, an identifier of the motor vehicle component can correspond to a particular electronic model, for example, an electronic model to generate a copy of the motor vehicle component corresponding to the identifier, stored in a data store (e.g., data store 130).

In some examples, a manufacturer (e.g., OEM or non-OEM) of a motor vehicle component can be displayed. For example, a manufacturer of each of a plurality of motor vehicle components included a particular motor vehicle (e.g., mobile device 102) can be displayed. The display can include a total number of OEM motor vehicle components (e.g., a percentage of OEM motor vehicle components) and/or a total number of non-OEM (e.g., a percentage of non-OEM motor vehicle components), among other information. Such a display can occur at a display within the particular motor vehicle and/or at a display external to the motor vehicle, such as those described herein. Displaying the manufacturer for the motor vehicle component and/or each of the plurality of motor vehicle components can readily enable a user to identify information such as a total number of OEM components in a motor vehicle and/or assist a user or system in generating motor vehicle components.

Information associated with the motor vehicle component, such as specifications of the motor vehicle component, can be used to create a 3D electronic model of the motor vehicle component. A 3D electronic model refers to a data representation of a motor vehicle component based on information associated with a motor vehicle component. The representation can be mathematical, and can include a collection of points in a 3D space that can be connected by various geometric connectors. Such geometric connectors can include, for example, triangles, lines, and curved surfaces, among other geometric connectors. That is, 3D electronic models can include solid models and/or shell models, among other types of electronic models. Solid models refer to electronic models that define a volume of the motor vehicle component they represent. Solid models can be formed, for example, using constructive solid geometry, among other techniques. Shell models refer to electronic models of a surface (e.g., a boundary) of a motor vehicle component they represent.

Electronic models can be created manually and/or automatically (e.g. through use of procedural modeling and/or based on reflected acoustic energy reflected from a motor vehicle component). For example, an electronic model can be created automatically based upon a two dimensional image (e.g., a photo) using triangulation, approximation, and/or other suitable mathematic techniques to create an electronic model therefrom.

The mobile device 102 can include a display 115 and/or the generating machine can include a display. The display can be included in the generating machine, or connected thereto, to display information (e.g., to a user of generating machine). Similarly, the display can be included in the mobile device 102, or connected thereto, to display information (e.g., to a user of the mobile device). A display can include a screen, for example, a graphical user interface (GUI) 114 that can provide (e.g., display and/or present) information to a user of generating machine. For example, the display can be used to display a GUI to digitally represent information and/or receive an input provided via the display (e.g., via a user interface). The display may be for example, a liquid crystal display (LCD), however, any appropriate display device and/or screen may be used. Further, generating machine can include any number of displays.

A display (e.g., display 115) can, in some embodiments, provide an indication of an expected life time of a motor vehicle component. In some embodiments, the display can provide a simultaneous display of a plurality of electronic representations indicative of respective expected life times for each of the plurality of motor vehicle components. Such a display can enable readily identifying component of the plurality of motor vehicle components that are within a threshold amount of time of satisfying the expected life and/or motor vehicle components that have exceeded their expected life. Expected or remaining service life can be used to prorate the value of various vehicle components. Readily identifying such motor vehicle components can promote dispositioning a motor vehicle based on damage suffered by the one or more motor vehicle components as described herein.

An indication refers to a visual, auditory, or other sensory output that can provide an indication of various pieces of information. The information from the indication can, in some embodiments include, information indicative of when an indication of damage to a motor vehicle component is received, an indication of initiation of generation of a motor vehicle component, indicative of an expected life of a motor vehicle component among the plurality of motor vehicle components, an indication of completion of generation of a motor vehicle component, and/or valuations associated with the vehicle or vehicle components (e.g., cost of new OEM part, cost of serviceable replacement part, cost of repair, cost of vehicle as equipped, et cetera) among other indications.

In some embodiments, an indication related to detected damage includes a total loss status of the motor vehicle. A total loss refers to a determination (e.g., based upon information particular to a type of motor vehicle or a specific motor vehicle stored in the data store 130) that a cost associated with repair/replacement (e.g., of each damaged component of the plurality of components) meets or exceeds a threshold value (e.g. a value of an insurance policy covering the motor vehicle having the indication of damage). The threshold can be a repair/scrap threshold, where a repair cost is identified at or below which the vehicle will be repaired, and above which the vehicle will be scrapped as a total loss. In alternative embodiments the discrete threshold can be inclusive to scrapping the vehicle as opposed to repairing it.

The repair/scrap threshold can be captured in a number of different static or dynamic values. In one example, a ratio of an amount of damage (e.g., a sum value associated with repair of the damage to and/or replacement of each the damaged motor vehicle components included in the motor vehicle) to a total value of the motor vehicle 10 can be determined. If such a ratio meets and/or exceeds a predetermined ratio than the motor vehicle can be determined to be a total loss ("scrap"). If the ratio does not meet and/or exceed the predetermined ratio of value, the motor vehicle can be determined not to be a total loss ("repair"). In an alternative aspect, the threshold can be a discrete residual value (e.g., $4,000, $10,000, $1,000), such that when the cost of the repairs is subtracted from the cost of the vehicle amounts below the discrete residual value will be treated as a total loss. These values can be common to groups of vehicles or vary by type of vehicle (e.g., rare and collectible sports car worth repairing given lower discrete residual value than extremely common sedan).

Ratios, discrete values, or other thresholds can also be modified by a location or type of damage. In this regard, a weight factor can be applied to the cost of repair or other values. For example, damage to quarter panels, even if substantial or expensive, may be weighted lower than damage to an engine block, given the disparity of repair complexity and the intangible costs associated with lengthy or difficult repairs and/or extended loss of a drive-able vehicle. In another example, extensive passenger compartment damage or accidents involving serious injury may be weighted more substantially than hail damage. In still another example, where a particular portion of a vehicle which is undamaged has a high salvage value, the repair costs to the damaged portions may be weighted to favor salvaging the valuable portion and more rapidly concluding dispositioning.

The value of the motor vehicle can be determined based on actuarial tables or commercial valuation products for similar vehicle makes, models, and years. The value of the motor vehicle can be dynamic and modified based on known information about the vehicle, such as mileage, condition (including specific damage or modifications), location, et cetera. Vehicle value may also be modified by prorating vehicle value (or the value of a portion of the vehicle) based on remaining service life as described herein.

Once comparison is complete, determining a total loss can enable comparatively quick payment to policy holders (e.g., those who own a policy covering a motor vehicle determined to be a total loss) and/or promote quick resolution of insurance claims (e.g., delivering a motor vehicle determined not to be a total loss to a repair facility to enable repair thereof relatively quickly). In embodiments, valuations and threshold compliance or noncompliance can be communicated to a variety of parties, including a vehicle owner, an insurer, repair shops, parts distributors, vehicle rental businesses, vehicle sale businesses, et cetera.

The mobile device 102 can include a network interface 119. The network interface 119 can, for example, include a receiver and/or a transceiver (e.g., wired and/or wireless), among other components suitable for communication with a network 120 (e.g., a mobile communications network). The network interface 119 can transmit an indication of detected damage (e.g., an amount of damage), for instance, to a mobile device and/or a data store, among other locations to promote detecting damage.

The network interface 119 can connect the mobile device 102 and/or the generating machine to a network 120. Network 120 can be a wired or wireless network, such as, for instance, a wide area network (WAN) such as the Internet, a local area network (LAN), a personal area network (PAN), a campus area network (CAN), or metropolitan area network (MAN), among other types of networks. As used herein, a "network" (e.g., network 120) can provide a communication system that directly or indirectly links computers and/or peripheral devices and allows users to access resources on other computing resources (e.g., generating machines and/or data stores, et cetera) and/or exchange messages with other users.

The network 120 can allow users to share resources on their own systems with other network users and to access information on centrally located systems or on systems that are located at remote locations. For example, the network 120 can permit communication with a mobile device, such as mobile device 102. The network 120 may provide connections to the Internet and/or to the networks of other entities (e.g., organizations, institutions, et cetera). Users may interact with network-enabled generating machine applications to make a network request, such as to get a file (e.g., a file of an acoustic baseline of motor vehicle 10 or a repair/scrap threshold associated with motor vehicle 10). Such network-enabled generating machine applications can also communicate with network management software, which can interact with network hardware to transmit information between devices on the network.

A mobile device 102, such as those described herein, can be coupled directly (e.g., via a cord) and/or indirectly (e.g., wirelessly) to the data store 130, and/or a mobile device 102. A mobile device, as used herein, can include a mobile telephone, a tablet, a mobile personal computer, and/or a personal digital assistant (PDA), among other mobile devices. For example, mobile device 102 can, in some embodiments, be coupled via a wire and/or wirelessly (e.g., via network 120) to a transceiver included in the generating machine to receive information (e.g., acoustic baseline information) via the transceiver from a data store, such as data store 130. That is, although FIG. 1 illustrates a single data store external from the mobile device 102 the present disclosure is not so limited. The data store 130 can include a number of data stores at a number of locations, for example, included within the generating machine, a shop, a mobile device 102, and/or at a location associated with an insurance provider, among other locations suitable for generating motor vehicle components, as described herein.

Figure 2:
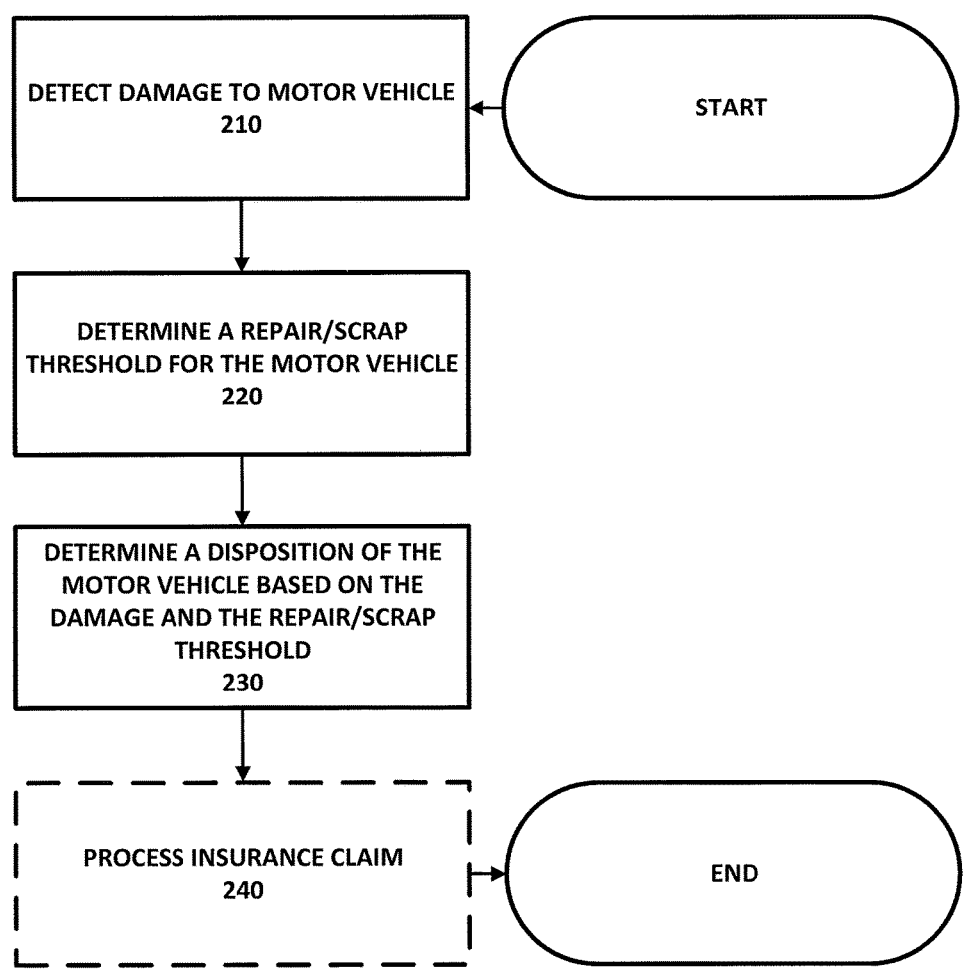
FIG. 2 illustrates a block diagram illustrating an example of a method to detect damage to a motor vehicle and disposition the motor vehicle for repair or scrap according to one or more embodiments of the present disclosure.

FIG. 2 illustrates a block diagram of an example of a method to detect damage according to one or more embodiments of the present disclosure. In various embodiments, the method can include detecting, via a sensor operatively connected to a mobile device, an amount of damage to a motor vehicle component of the motor vehicle, as shown at block 210. Detecting can include executing instructions stored in memory (e.g., memory 106) to detect an amount of damage to a motor vehicle component of the motor vehicle. Similarly, block 210 can include executing instructions stored in memory to perform the examples of the method described therein. Such a sensor can be analogous or similar to the sensor, motor vehicle component, and/or motor vehicle as described with respect to FIG. 1. Similarly, the data store, among others, can be analogous or similar to the data store 130 described with respect to FIG. 1.

In some embodiments the method for detecting damage can include displaying the indication of the amount of damage to the motor vehicle component. For instance, the displaying can occur via a display, such as the display described with respect to FIG. 1.

In some embodiments, displaying can include displaying a total loss status. The total loss status refers to a disposition determination (e.g., a current determination) of whether the motor vehicle 10 is a total loss. A particular color, symbol, letter, collection of letters, among other possible displays can be provided via a display to indicate a total loss status. For example, a "no" display could indicate the total loss status is not present. Similarly, a "yes" display could indicate the total loss status is present. Such a display, can readily enable an individual to determine a proper course of action regarding the motor vehicle. For instance, whether the motor vehicle 10 should be repaired/replaced when the total loss status is not present or treated otherwise when the total loss status is present (e.g., subdivided into constituent parts which may be resold).

In various embodiments, the method can optionally include processing (e.g., automatically processing) an insurance claim, as described herein, based on the amount of damage to the motor vehicle component, as shown at block 240. In some embodiments, the method can include receiving an indication of damage to a motor vehicle component included in a motor vehicle. Such an indication, can in some embodiments, cause the generation of a motor vehicle component (e.g., generation of a 3D copy of the motor vehicle component indicated as damaged). In some embodiments, the method can include displaying an expected life, as described herein, of the generated motor vehicle component.

Figure 3:
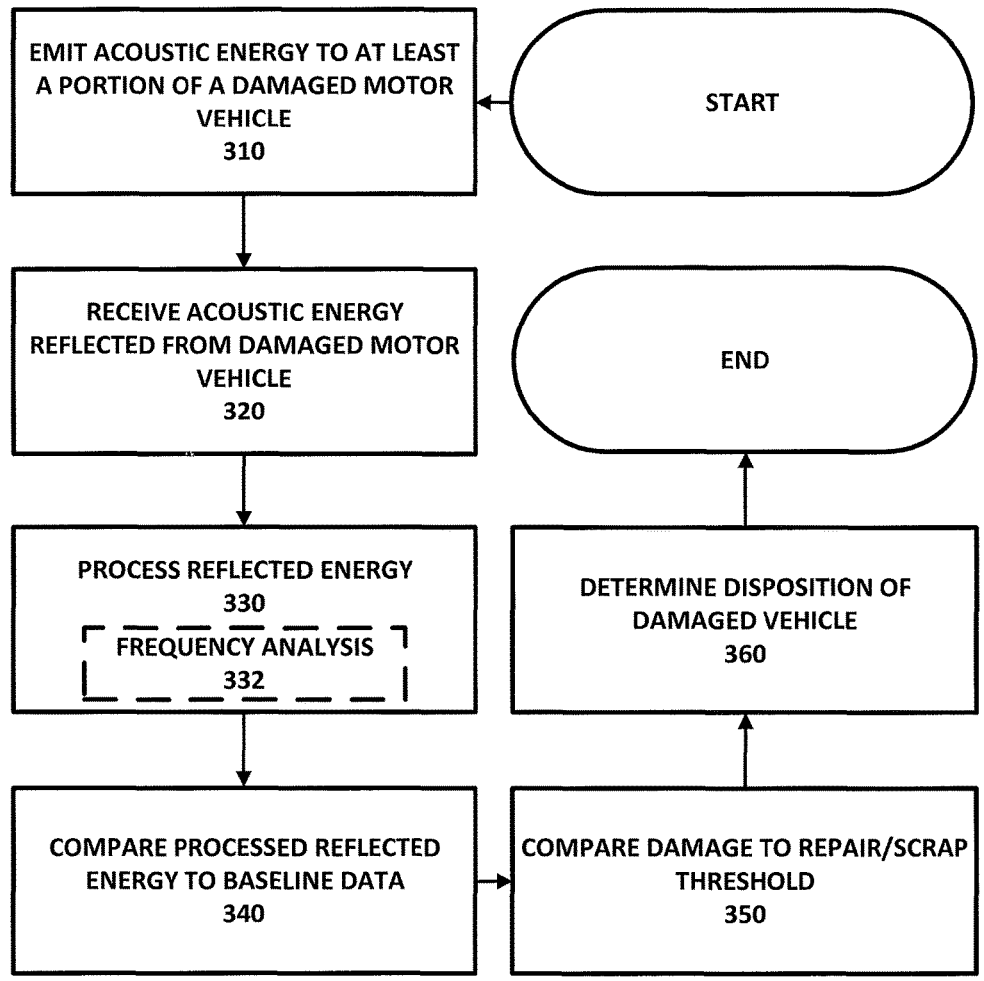
FIG. 3 illustrates a block diagram illustrating an example of instructions to detect damage to a motor vehicle and disposition the motor vehicle for repair or scrap according to one or more embodiments of the present disclosure.

FIG. 3 illustrates a block diagram illustrating an example of instructions to detect damage according to one or more embodiments of the present disclosure. As illustrated in block 310, the instructions can, in various embodiments, include instructions executable by a processor to issue acoustic energy into a vehicle to determine an amount of damage to a motor vehicle component of the motor vehicle. In some embodiments, the instructions to detect can include instructions to detect an amount of damage to the mechanical system, such as those described herein.

The instructions (e.g., machine readable instructions 110, as described in FIG. 1) can include instructions to receive reflected acoustic energy from the motor vehicle, as illustrated at block 320. In some examples, the reflected acoustic energy can provide an indication of damage to a mechanical system of a motor vehicle, for example, an indication of a detected amount of damage to the mechanical system like the frame of the motor vehicle.

As illustrated at block 330, the instructions can include instructions executable by the processor to process the reflected acoustic energy to assess the damage to the motor vehicle. This can be done through frequency analysis, as shown with box 332. The results of the acoustic energy processing can be compared to a baseline of acoustic response from the vehicle, such a baseline retrieved from data store 130 or from memory 106. The processed reflected acoustic energy can be compared to a baseline level, as shown with box 340, to determine the character and extent of damage by comparing the processed reflected energy to baseline data. Using the character and extent of damage determined at 340, a comparison can be made to the repair/scrap threshold at 350 to determine whether the damage is efficient to repair or if the damaged vehicle should be dispositioned as a total loss. If the determination at 350 returns that the repair cost is below the threshold for scrapping the damaged vehicle, at 360 a determination is made to disposition the vehicle to a repair facility. If the determination at 350 returns that the repair cost is above the threshold for scrapping the damaged vehicle, at 360 a determination is made to disposition the vehicle as a total loss.

In some embodiments, the instructions to store can include instructions to transmit a Short Message Service (SMS) message to a mobile device, such as those described herein. Such a transmission can assist a user of a motor vehicle in discovering that damage has been detected. For example, should a motor vehicle component of a motor vehicle incur damage (e.g., be subjected to a collision) while the user of the motor vehicle is at another location such a transmission can assist the user in discovering the damage has been detected, as described herein, without the user having to be present at the same location as the motor vehicle.

In some embodiments, the instructions can include instructions to process an insurance claim based on the indication of damage. For instance, an amount of damage, detected as described herein, can correspond to an estimate cost to fix the amount of damage included in an insurance claim. Processing refers to calculation of such a cost, storage of such a cost in a database, comparing such a cost to policy information (e.g., a deductible and/or policy limits), and/or payment of such a cost (e.g., to a policyholder), among others processing acts to generally associated with an insurance claim. For example, in some embodiments, processing an insurance claim can include requesting generation of a replacement motor vehicle component (e.g., to replace a damaged motor vehicle component).

As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate the embodiments of the present disclosure and should not be taken in a limiting sense. As used herein, "a" or "a number of" used in referring to a particular thing is intended refer to one or more such things.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, if provided, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim. Rather, inventive subject matter lies in less than all features of a single disclosed embodiment. Thus, the claims, if provided, are hereby incorporated into the Detailed Description, with each claim standing on its own as a separate embodiment.

What is claimed:

1. A system for detecting damage, comprising:
   a sensor to detect damage to a motor vehicle;
   a network interface communicative with a data store, wherein the data store includes baseline acoustic response information associated with the motor vehicle;
   a processor operatively connected to the network interface and the sensor, and communicative connected with a memory having instructions recorded thereon that, when read by the processor, cause the processor to:
   cause the sensor to issue acoustic energy toward the motor vehicle and receive reflected acoustic energy therefrom;
   receive acoustic response data related to the motor vehicle subsequent to damage, wherein the acoustic response data is collected by the sensor;
   compare the received acoustic data to the baseline acoustic response information associated with the motor vehicle to determine an amount of damage to the motor vehicle;
   determine a repair/scrap threshold for the motor vehicle; and
   determine a disposition of the motor vehicle based on the amount of damage to the motor vehicle and the repair/scrap threshold.

2. The system of claim 1, wherein the data store includes a repair/scrap disposition threshold particular to the motor vehicle.

3. The system of claim 1, wherein the instructions further cause the processor to process an insurance claim using the determined disposition of the motor vehicle.

4. The system of claim 1, wherein the instructions recorded on the memory further cause the processor to perform frequency analysis on the received reflected acoustic energy.

5. A non-transitory computer-readable medium storing instructions executable by a processor to:
   cause a sensor to issue acoustic energy toward a motor vehicle and receive reflected acoustic energy therefrom;
   receive acoustic response data related to the motor vehicle subsequent to damage, wherein the acoustic response data is collected by the sensor;
   compare the received acoustic data to baseline acoustic response information associated with the motor vehicle to determine an amount of damage to the motor vehicle;
   determine a repair/scrap threshold for the motor vehicle; and
   determine a disposition of the motor vehicle based on the amount of damage to the motor vehicle and the repair/scrap threshold.

6. The non-transitory computer-readable medium of claim 5, wherein the instructions include instructions executable by the processor to determine an amount of damage to a frame of the motor vehicle.

7. A method of dispositioning a motor vehicle, comprising:
   receiving acoustic response data related to a motor vehicle subsequent to damage, wherein the acoustic response data is collected by a sensor;
   comparing the received acoustic data to baseline acoustic response information associated with the motor vehicle to determine an amount of damage to the motor vehicle;
   determining a repair/scrap threshold for the motor vehicle; and
   determining a disposition of the motor vehicle based on the amount of damage to the motor vehicle and the repair/scrap threshold.

8. The method of claim 7, including displaying an indication of the disposition of the motor vehicle.

9. The method of claim 7, wherein the repair/scrap threshold is based on at least one of information from a data store and characteristics of the motor vehicle before damage was incurred.

10. The method of claim 9, wherein the characteristics of the motor vehicle before damage was incurred includes a remaining service life of a motor vehicle component.

11. The method of claim 7, wherein the repair/scrap threshold is calculated dynamically for the motor vehicle based.

\* \* \* \* \*